United States Patent
Xu et al.

(10) Patent No.: US 8,408,046 B2
(45) Date of Patent: Apr. 2, 2013

(54) SYSTEM AND METHOD FOR IN LINE IN SITU VALIDATION OF EXHAUST FILTERS

(76) Inventors: Zhonglin Xu, Beijing (CN); Yizhao Zhang, Beijing (CN); Feng Wen, Beijing (CN); Jinming Shen, Shanghai (CN); Xin Feng, Beijing (CN); Rajagopal Vijayakumar, Liverpool, NY (US)

( * ) Notice: Subject to any disclaimer, the term of this patent is extended or adjusted under 35 U.S.C. 154(b) by 566 days.

(21) Appl. No.: 12/617,996

(22) Filed: Nov. 13, 2009

(65) Prior Publication Data

US 2010/0116031 A1   May 13, 2010

Related U.S. Application Data

(60) Provisional application No. 61/114,297, filed on Nov. 13, 2008.

(51) Int. Cl.
*G01N 15/08* (2006.01)
(52) U.S. Cl. .......................................................... 73/38
(58) Field of Classification Search ...................... 73/38
See application file for complete search history.

(56) References Cited

U.S. PATENT DOCUMENTS

| | | | |
|---|---|---|---|
| 2007/0044438 A1* | 3/2007 | Morse et al. | 55/342 |
| 2008/0087074 A1* | 4/2008 | Morse et al. | 73/38 |

* cited by examiner

*Primary Examiner* — Hezron E Williams
*Assistant Examiner* — Paul West
(74) *Attorney, Agent, or Firm* — Frederick J. M. Price; George R. McGuire; Bond Schoeneck & King

(57) ABSTRACT

A system for in line in situ validation of an air filter of an exhaust filter system including a scan head, a means for facilitating movement of said scan head in the XY plane, a means for externally controlling the movement of the scan head from outside the plenum of the exhaust filter system in the XY plane, and a means for coupling the scan head to the means for externally controlling the movement of the scan head, is provided. The system can also include a scanning arm, inside and outside magnetic couples, and rolling means to facilitate movement of the inside and outside magnetic couples. A method for in line in situ validation of an air filter in an exhaust filter system is also described, which involves the use of the system for in line in situ validation of air filters of an exhaust filter system.

6 Claims, 4 Drawing Sheets

SYSTEM AND METHOD FOR IN LINE IN SITU VALIDATION OF EXHAUST FILTERS

RELATED APPLICATION

The present application claims priority to U.S. provisional patent application No. 61/114,297, filed on Nov. 13, 2008, which is hereby incorporated by reference herein in its entirety.

BACKGROUND OF THE INVENTION

1. Field of Invention

The present invention relates generally to a system and method for testing and validating the integrity of air filters, and, more particularly, to a system and method for in line in situ validation of air filters of an exhaust filter system.

2. Description of Prior Art

Cleanliness of air supplied and exhausted from containment equipment such as Biological Safety Cabinets or Bio Safety Cabinets ("BSC"), lab hoods, bag in bag out systems, etc., depend on the integrity of air filters installed to remove contaminants. Particle contaminants are typically removed by using high efficiency air filters.

Standard operating protocols require that these air filters be tested periodically to ensure that they are leak free. Typically, this validation testing requires the shutting down of the operations of the containment equipment to gain access to the filter. The integrity of the filter is verified by challenging the filter with an aerosol and checking for leaks by scanning the face of the filter. Since hazardous materials are often handled in these containment equipment, validation of filters will typically necessitate decontamination prior to accessing the filter for testing.

A manual method for testing the integrity of air filters of an exhaust filter system has been used. In the manual method, a filter is scanned with a manually movable sampling head operated via gloves mounted on the chamber. The gloves separate the outside and the operator from the contaminants inside the chamber.

As seen in FIGS. 1A-D, a current automatic scanning system for testing the integrity of air filters of an exhaust filter system is shown. Components of this scanning system for testing filters are included within the filter housing/chamber. In particular, FIGS. 1A-D show a conventional exhaust filter system 100, where contaminated air is exhausted from an exhaust duct 120 through a filter 130 housed in a plenum 110. An exhaust outlet 140 is also shown. Since all such systems 100 have an exhaust plenum 110, it is possible to use the space to install an air sampling inlet, also known as a scanning head/sampling probe 150, inside the plenum 110. This allows for scanning of the filter 130 for leaks without actually accessing the filter 130. The scan head 150 can be automatically moved in both the X and Y directions by a traditional XY coordinate system (scan mechanism) 160 or by a set of racks and pinions (not shown), which are also within the exhaust plenum 110. FIG. 1C further shows multiple sampling probes 150 coupled in a row connected to scanning arms 155, and FIG. 1D shows one large sampling cylinder 150' with several sampling holes or slits installed within the scanning arm 155'. The sampling probes 150 and sampling cylinder 150' are used for scanning the entire downstream face of the installed filter to determine leaks. An optical particle counter ("OPC"), and an exhaust stack tube 111 are also shown.

With respect to current automatic systems, the entire XY traverse gear is enclosed inside the plenum 110 and mounted on an XY traverse mechanism that is fixed on the inside of the back plate 115 of the inside of the plenum 110 with only the electric and sample connection leading outside via sealed grommets (not shown). When needed, the XY traverse system can be powered and the filter can be scanned.

SUMMARY OF THE INVENTION

The present invention recognizes that there are potential problems and/or disadvantages with the above-referenced current methods and systems for testing the integrity of air filters of an exhaust filter system. One potential problem is that housing the complicated scanning systems within the exhaust plenum, as required for the conventional type of automated sampling, not only adds to the size and costs of the unit, but also increases the costs for cleanup and maintenance. This is because these current scanning systems are continuously exposed to the contamination and air flow. In addition, in some cases, the size of the equipment may be too large requiring extra containment housing. This leads to problems of over-complicating the system (more particle counters for aerosol measurements, such as the type shown in FIG. 1C), and impossibility of locating the local defect, such as the type shown in FIG. 1D. Various embodiments of the present invention may be advantageous in that they may solve or reduce one or more of the potential problems and/or disadvantages discussed above in this paragraph.

It is therefore a principal object and advantage of the present invention to overcome the shortcomings of the prior art.

It is an additional object and advantage of the present invention to provide a system and method for in line in situ validation of air filters of an exhaust filter system that can avoid any need for decontamination.

It is a further object and advantage of the present invention to provide a system and method for in line in situ validation of air filters of an exhaust filter system that can allow for in line testing of filters.

It is another object and advantage of the present invention to provide a system and method for in line in situ validation of air filters of an exhaust filter system that takes advantage of the cover plate of the plenum to install a scan head within the plenum that can be controlled externally, avoiding the need for complicated gear trains inside the plenum.

In accordance with the foregoing objects and advantages, an embodiment of the present invention provides a system for in line in situ validation of air filters of an exhaust filter system which can include a scan head (which is a device that includes a sample probe or sampling device), which can be enclosed within a plenum of an exhaust filter system, a means for moving the scan head in the XY plane, a means for externally controlling (i.e., outside the plenum) the movement of the scan head (i.e., the XY traverse mechanism) in the XY plane, and a means for coupling the scan head to the means for externally controlling the movement of the scan head (such as a magnetic connection).

In accordance with an alternative embodiment of the present invention, a system for in line in situ validation of an air filter of an exhaust filter system is provided which can include, but is not limited to, a sample probe/scan head adapted to be enclosed within a plenum of an exhaust filter system, wherein the plenum includes a face plate; a scanning arm mechanically connected to the sample probe; an inside magnetic coupling (referred to herein as "couple") mechanically connected to the scanning arm; at least one inside rolling means (i.e., rolling means that are inside the plenum) mechanically connected to the inside magnetic couple, and adapted to roll on the inside of the face plate. Directly opposite the inside rolling means and mechanically/electrically connected to the inside rolling means/inside magnetic couple is at least one outside rolling means (i.e., rolling means that are outside the plenum), and an outside magnetic couple mechanically connected to the at least one outside rolling means, where the outside rolling means is adapted to roll on the outside of the face plate. The outside magnetic couple is also mechanically connected to a means for externally controlling movement of the scan head outside the plenum.

In accordance with an embodiment of the present invention, a method for in line in situ validation of air filters in an exhaust filter system is provided. The method involves the use of the embodiments of the system for in line in situ validation of air filters of an exhaust filter system as described supra.

BRIEF DESCRIPTION OF THE DRAWINGS

The present invention will be more fully understood and appreciated by reading the following Detailed Description in conjunction with the accompanying drawings, in which.

DETAILED DESCRIPTION

Figure 1A:
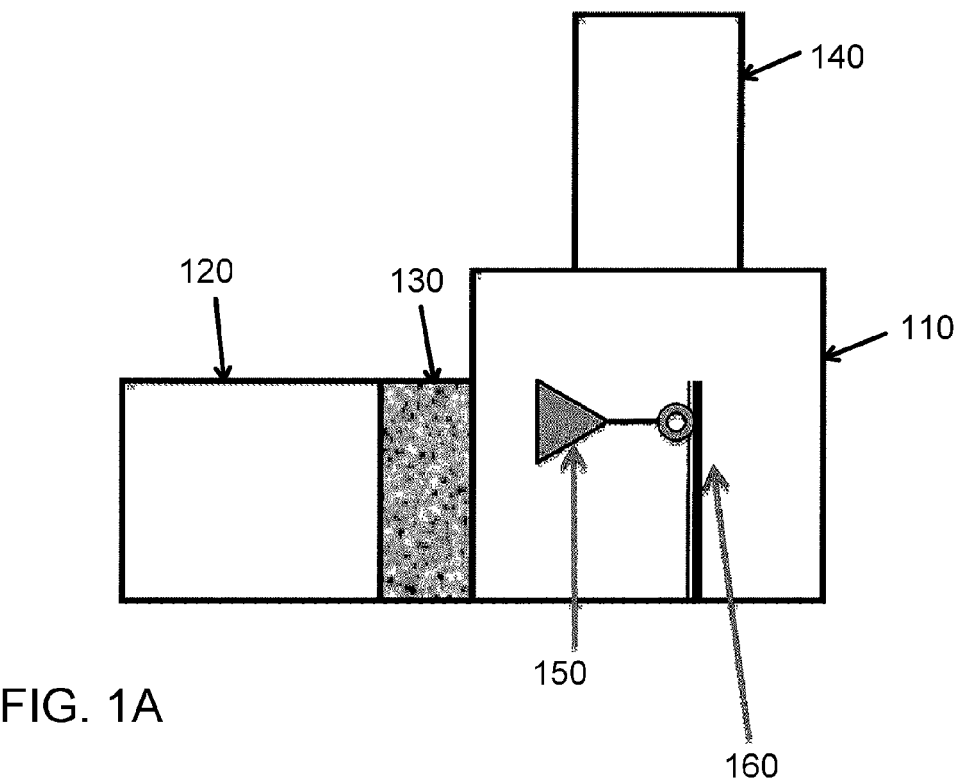
FIG. 1A is an elevation view illustrating a conventional scanning system for testing the integrity of air filters of an exhaust filter system.
Figure 1B:
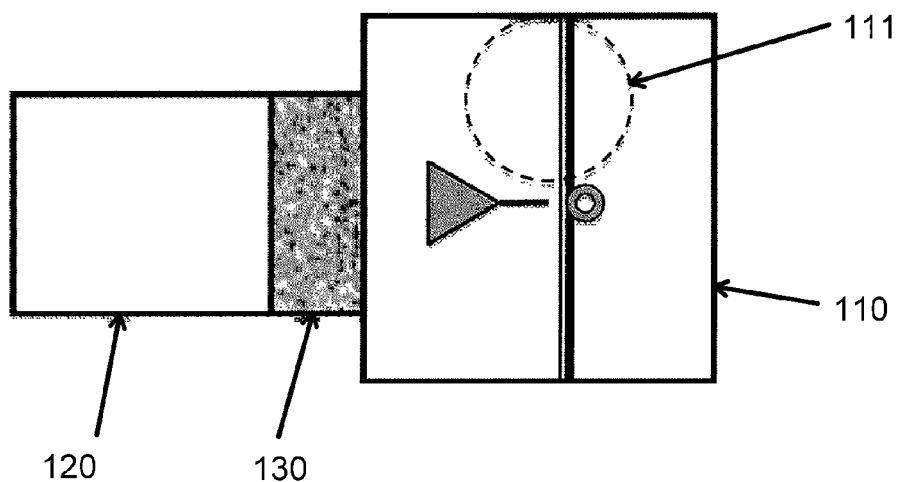
FIG. 1B is a plan view illustrating a conventional scanning system for testing the integrity of air filters of an exhaust filter system.
Figure 1C:
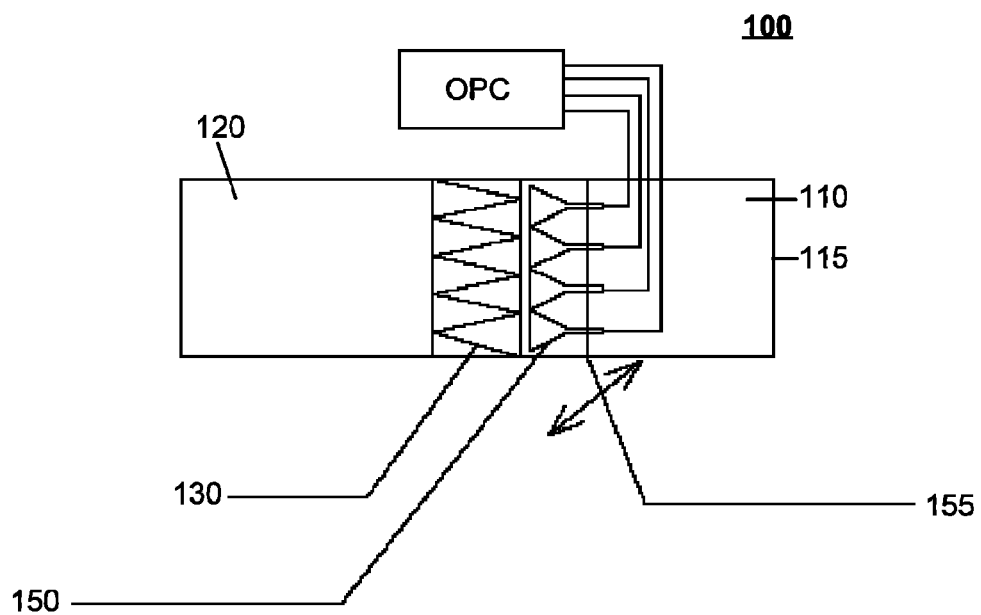
FIG. 1C is a plan view illustrating a conventional scanning system for testing the integrity of air filters of an exhaust filter system.
Figure 1D:
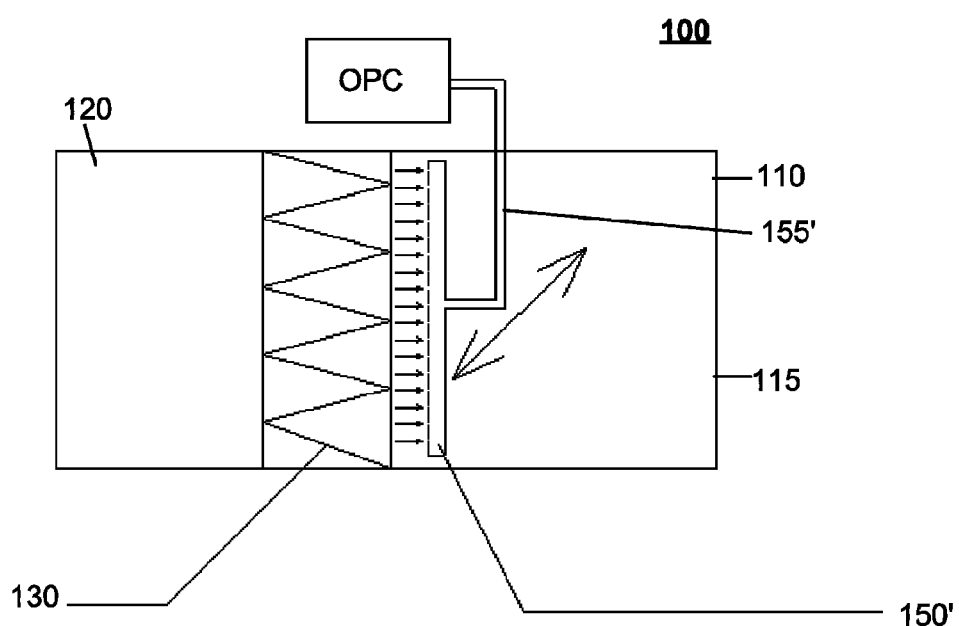
FIG. 1D is a plan view illustrating a conventional scanning system for testing the integrity of air filters of an exhaust filter system.

Reference will now be made in detail to the present preferred embodiments of the invention, wherein like reference numerals refer to like components, examples of which are illustrated in the accompanying drawing.

Figure 2:
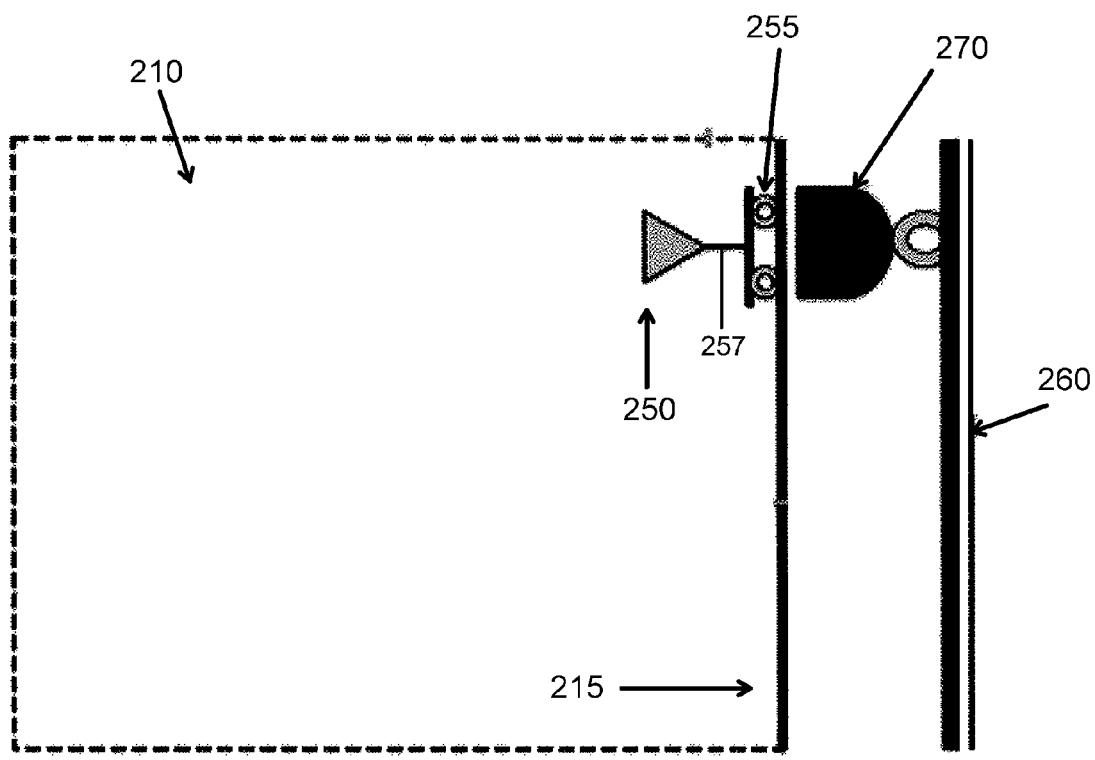
FIG. 2 is a plan view illustrating a system for in line in situ validation of air filters of an exhaust filter system, in accordance with an embodiment of the present invention.

Turning to FIG. 2, a plan view illustrating a system for in line in situ validation of air filters in an exhaust filter system is shown, in accordance with an embodiment of the present invention. The system includes, but is not limited to, a scan head/sample probe 250, a scanning arm 257, means for facilitating movement of the scan head in the XY plane 255 (such as at least one caster or roller, preferably a plurality of casters/rollers connected to a mounting plate, where either the mounting plate or the caster/roller can be magnetic; as understood by those skilled in the art, casters can roll in all directions, and rollers can roll in two directions, e.g., north and south or left and right, etc.), a means for externally controlling 260 (i.e., outside the plenum 210 of the exhaust filter system 200) the movement of the scan head 250 in the XY plane (e.g., a mechanical XY traverse system), and means for coupling 270 the scan head 250 to the means for externally controlling 260 the movement of the scan head 250. The means for coupling 270 (which can be a magnet) can couple the scan head 250 (e.g., through the magnetic plate) to the means for externally controlling 260 by any mechanical (preferably magnetic) and/or electrical connection. This coupling of the scan head 250 to the means for externally controlling 260 the movement of the scan head 250 allows for controlling the movement of the scan head 250 from outside the plenum 210.

In accordance with an embodiment of the present invention, a system for in line in situ validation of air filters is provided that takes advantage of the plenum 210 to install parts of a scanning system inside it, with connections to an internal or external particle sampling instrument (not shown), as well as a means for externally controlling 260 the movement of the scan head 250 in the XY plane. That is, the scan head 250 can sweep over the entire face of the filter (not shown) to test for leaks. The air sampled through the scan head 250 can be connected via a hose to an external particle counter (not shown) to determine whether the performance of the filter is within acceptable limits as the scan head 250 sweeps over the face of the filter.

In accordance with an embodiment of the present invention, a method for in line in situ validation of air filters in an exhaust filter system is provided. The method involves the use of embodiments the system for in line in situ validation of air filters of an exhaust filter system as described herein. For proper scanning of an air filter, the scan head 250 should perform sequential traverses at a predetermined and uniform rate across the face of the filter until the entire face of the filter has been scanned. This is similar to the way one mows one's lawn by traversing back and forth across the entire grounds.

Figure 3:
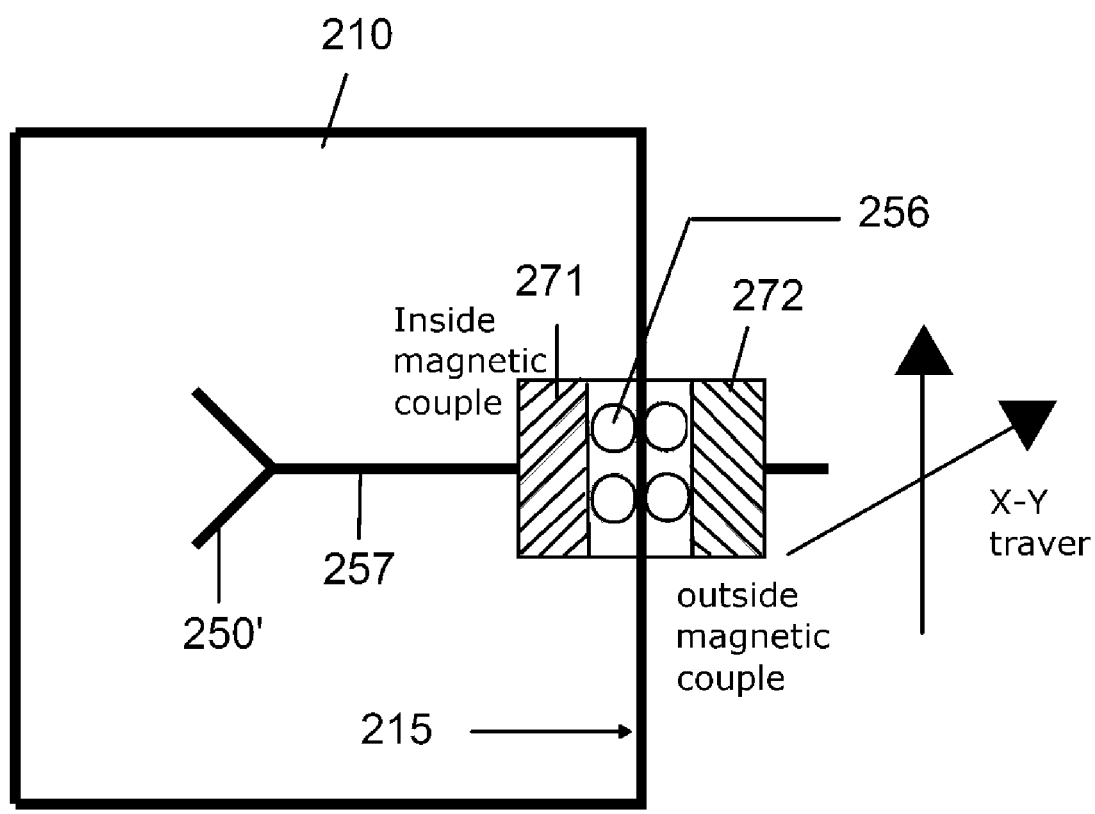
FIG. 3 is a plan view illustrating a system for in line in situ validation of air filters of an exhaust filter system, in accordance with an embodiment of the present invention.

In accordance with an embodiment of the present invention and in contrast to the conventional system, the XY traverse system is externally mounted to the plenum 210, as shown in FIG. 2 (and in FIG. 3, as described infra). The scan head 250 can preferably be magnetically coupled to the external XY traverse mechanism 260 (preferably through a magnetic coupling 270). This set up can be further enhanced by setting the scan head 250 on castors 255 that roll on the face plate 215 of the plenum 210 for effortless movement of the scan head 250, through which it can be magnetically connected to the external XY traverse system 260. The scan head 250 can be mechanically connected to a scanning arm 257, which can be mechanically connected to the casters 255 that are adapted to roll on the inside of the face plate 215 (alternatively, the casters may be on the outside of the face plate 215). The magnetic coupling of the scan head 250 to the external XY traverse system 260 also permits the manual scanning without the need for access to the filter. More than one scan head 250 with more than one scanning arm 257 can be used.

FIG. 3 is a plan view illustrating a system for in line in situ validation of air filters of an exhaust filter system, in accordance with an alternative embodiment of the present invention. The system includes but is not limited to, a sample probe/scan head 250', a scanning arm 257' mechanically connected to the sample probe 250' and to an inside magnetic couple 271 (i.e., inside the plenum). The inside magnetic couple 271 can be mechanically/electrically connected to at least one inside rolling means 255' (preferably a plurality of rolling means, e.g., balls, casters, which can, but does not have to be magnetic), which roll on the inside of the face plate 215 inside the plenum 210. Directly opposite and mechanically/electrically connected to the at least one inside magnetic couple 271 and/or inside rolling means 255' on the outside of the face plate 215 on the outside of the plenum 210 is at least one outside rolling means 256 (preferably a plurality of rolling means, e.g., balls, casters, which can, but does not have to be magnetic), and an outside magnetic couple 272 (i.e., outside the plenum). The outside magnetic couple 272 can be mechanically/electrically connected to the at least one outside rolling means 256, and can be mechanically/electrically connected to an XY traverse system 260' (not shown). More than one sample probe 250' with more than one scanning arm 257' can be used.

While the invention is susceptible to various modifications, and alternative forms, specific examples thereof have been shown in the drawing and are herein described in detail. It should be understood, however, that the invention is not to be limited to the particular forms or methods disclosed, but to the contrary, the invention is to cover all modifications, equivalents and alternatives falling within the spirit and scope of the claimed invention.

Definitions

Any and all published documents mentioned herein shall be considered to be incorporated by reference, in their respective entireties, herein to the fullest extent of the patent law. The following definitions are provided for claim construction purposes:

Present invention: means at least some embodiments of the present invention; references to various feature(s) of the "present invention" throughout this document do not mean that all claimed embodiments or methods include the referenced feature(s).

First, second, third, etc. ("ordinals"): Unless otherwise noted, ordinals only serve to distinguish or identify (e.g., various members of a group); the mere use of ordinals implies neither a consecutive numerical limit nor a serial limitation.

Embodiment: a machine, manufacture, system, process and/or composition that may (not must) meet the embodiment of a present, past or future patent claim based on this patent document; for example, an "embodiment" might not be covered by any claims filed with this patent document, but described as an "embodiment" to show the scope of the invention and indicate that it might (or might not) covered in a later arising claim (for example, an amended claim, a continuation application claim, a divisional application claim, a reissue application claim, a re-examination proceeding claim, an interference count); also, an embodiment that is indeed covered by claims filed with this patent document might cease to be covered by claim amendments made during prosecution.

Electrically Connected: means either directly electrically connected, or indirectly electrically connected, such that intervening elements are present; in an indirect electrical connection, the intervening elements may include inductors and/or transformers.

Mechanically connected: Includes both direct mechanical connections, and indirect mechanical connections made through intermediate components; includes rigid mechanical connections as well as mechanical connection that allows for relative motion between the mechanically connected components; includes, but is not limited, to welded connections, solder connections, connections by fasteners (for example, nails, bolts, screws, nuts, hook-and-loop fasteners, knots, rivets, quick-release connections, latches and/or magnetic connections), force fit connections, friction fit connections, connections secured by engagement caused by gravitational forces, pivoting or rotatable connections, and/or slidable mechanical connections.

To the extent that the definitions provided above are consistent with ordinary, plain, and accustomed meanings (as generally shown by documents such as dictionaries and/or technical lexicons), the above definitions shall be considered supplemental in nature. To the extent that the definitions provided above are inconsistent with ordinary, plain, and accustomed meanings (as generally shown by documents such as dictionaries and/or technical lexicons), the above definitions shall control. If the definitions provided above are broader than the ordinary, plain, and accustomed meanings in some aspect, then the above definitions shall be considered to broaden the claim accordingly.

To the extent that a patentee may act as its own lexicographer under applicable law, it is hereby further directed that all words appearing in the claims section, except for the above-defined words, shall take on their ordinary, plain, and accustomed meanings (as generally shown by documents such as dictionaries and/or technical lexicons), and shall not be considered to be specially defined in this specification. In the situation where a word or term used in the claims has more than one alternative ordinary, plain and accustomed meaning, the broadest definition that is consistent with technological feasibility and not directly inconsistent with the specification shall control.

Unless otherwise explicitly provided in the claim language, steps in method steps or process claims need only be performed in the same time order as the order the steps are recited in the claim only to the extent that impossibility or extreme feasibility problems dictate that the recited step order (or portion of the recited step order) be used. This broad interpretation with respect to step order is to be used regardless of whether the alternative time ordering(s) of the claimed steps is particularly mentioned or discussed in this document.

What is claimed is:

1. A system for in line in situ validation of an air filter of an exhaust filter system comprising:
    a sample probe adapted to be enclosed within a plenum of an exhaust filter system, wherein the plenum includes a face plate;
    an inside magnetic couple mechanically connected to said sample probe;
    at least one inside rolling means mechanically connected to said inside magnetic couple, and adapted to roll on the inside of the face plate; and
    a means for externally controlling movement of said scan head outside the plenum.

2. The system of claim 1, further comprising a plurality of inside rolling means.

3. The system of claim 1, further comprising a scanning arm mechanically connected to said sample probe.

4. The system of claim 1, further comprising at least one outside rolling means mechanically connected to said at least one inside rolling means or to said inside magnetic couple through the face plate, and adapted to roll on the outside of the face plate with said at least one inside rolling means.

5. The system of claim 4, further comprising a plurality of outside rolling means.

6. The system of claim 4, further comprising an outside magnetic couple mechanically connected to said least one outside rolling means, and to said means for externally controlling movement of said scan head outside the plenum.

* * * * *